(12) United States Patent
Clayton et al.

(10) Patent No.: US 7,348,022 B1
(45) Date of Patent: Mar. 25, 2008

(54) BIOMEDICAL COMPOSITION

(75) Inventors: Anthony Brian Clayton, Oakleigh (AU); Gordon Francis Meijs, Murrumbeena (AU)

(73) Assignee: Commonwealth Scientific and Industrial Research Organisation (AU)

( * ) Notice: Subject to any disclaimer, the term of this patent is extended or adjusted under 35 U.S.C. 154(b) by 307 days.

(21) Appl. No.: 10/048,700

(22) PCT Filed: Aug. 2, 2000

(86) PCT No.: PCT/AU00/00915

§ 371 (c)(1),
(2), (4) Date: May 6, 2002

(87) PCT Pub. No.: WO01/08603

PCT Pub. Date: Feb. 8, 2001

(30) Foreign Application Priority Data

Aug. 2, 1999 (AU) .................... PQ1978

(51) Int. Cl.
*A61F 13/00* (2006.01)
*A61F 2/00* (2006.01)
*C08F 283/00* (2006.01)

(52) U.S. Cl. ............... 424/427; 424/422; 424/429; 525/474

(58) Field of Classification Search ............ 424/423, 424/424, 400, 427, 422, 429; 525/474
See application file for complete search history.

(56) References Cited

U.S. PATENT DOCUMENTS

| | | | |
|---|---|---|---|
| 4,136,250 A | 1/1979 | Mueller | |
| 4,563,539 A | 1/1986 | Gornowicz | |
| 4,605,712 A * | 8/1986 | Mueller et al. ............ 525/474 |
| 4,616,045 A * | 10/1986 | Upchurch ................ 522/60 |
| 4,852,969 A * | 8/1989 | Babirad et al. ............ 385/143 |
| 5,079,319 A | 1/1992 | Mueller | |
| 5,233,007 A | 8/1993 | Yang | |
| 5,236,970 A | 8/1993 | Christ | |
| 5,246,979 A | 9/1993 | Lutz | |
| 5,278,258 A | 1/1994 | Gerace | |
| 5,346,946 A | 9/1994 | Yokoyama | |
| 5,376,694 A | 12/1994 | Christ | |
| 5,391,590 A * | 2/1995 | Gerace et al. ............ 523/107 |
| 5,411,553 A | 5/1995 | Gerace | |
| 5,420,213 A | 5/1995 | Yang | |
| 5,444,106 A | 8/1995 | Zhou | |
| 5,476,515 A * | 12/1995 | Kelman et al. ............ 623/6.59 |
| 5,494,946 A | 2/1996 | Christ | |
| 5,556,383 A | 9/1996 | Wang et al. ............ 604/96 |
| 5,610,257 A | 3/1997 | Richard et al. ............ 528/15 |
| 5,647,409 A | 7/1997 | Christ | |
| 5,661,195 A | 8/1997 | Christ | |
| 5,772,667 A | 6/1998 | Blake | |
| 5,869,549 A | 2/1999 | Christ | |
| 5,977,282 A | 11/1999 | Ebbrecht | |
| 6,066,172 A * | 5/2000 | Huo et al. ............ 623/6.56 |
| 6,277,147 B1 | 8/2001 | Christ | |
| 6,361,561 B1 | 3/2002 | Huo | |
| 6,399,734 B1 | 6/2002 | Hodd | |
| 2002/0082691 A1 | 6/2002 | Christ | |

FOREIGN PATENT DOCUMENTS

| | | |
|---|---|---|
| EP | 0293560 | 12/1988 |
| EP | 0335312 | 10/1989 |
| EP | 0578087 | 1/1994 |
| JP | 2002-128829 | 5/2002 |
| WO | WO 93/21245 | 10/1993 |
| WO | WO 00/22459 | 4/2000 |
| WO | WO 00/22460 | 4/2000 |
| WO | WO 01/17570 | 3/2001 |
| WO | WO 01/76651 | 10/2001 |
| WO | WO 01/81075 | 11/2001 |

OTHER PUBLICATIONS

Zelentsova, N.V., Zelentsov, S.V, Abadie, M.J.M and Makareeva, N "Photochemical crosslinking of the low molecular weight vinylcontaining polysiloxanes with organic azides". Phobiology 20002.

* cited by examiner

*Primary Examiner*—Michael G. Hartley
*Assistant Examiner*—Micah-Paul Young
(74) *Attorney, Agent, or Firm*—Andrus, Sceales, Starke & Sawall, LLP

(57) ABSTRACT

A method of preparing intraocular lenses in situ is disclosed. The method involves the injection of an unsaturated macromonomer of the formula

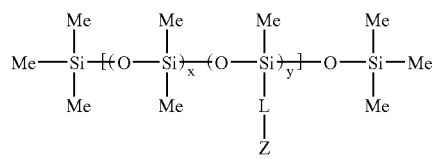

The macromonomer is then polymerized to give a polymer having an E modulus in the range 0.5-5 kPa.

27 Claims, No Drawings

BIOMEDICAL COMPOSITION

CROSS-REFERENCE TO RELATED APPLICATIONS

This application is the U.S. national stage application of International Application PCT/AU00/00915, filed Aug. 2, 2000, which international application was published on Feb. 8, 2001, as International Publication WO 01/08603 in the English language. The International Application claims priority of Australian Patent Application No. PQ 1978, filed Aug. 2, 1999.

TECHNICAL FIELD OF THE INVENTION

This invention relates to ethylenically unsaturated macromonomers that are suitable for use as precursors for polymers in biomedical applications.

BACKGROUND OF THE INVENTION

The use of polymeric prostheses and biomedical mouldings has grown rapidly in recent times. Such mouldings may be used for contact lenses or for specific ophthalmic purposes. For example, they may be used for intraocular lenses and eye bandages. They may also be used for surgical mouldings such as heart valves and artificial arteries. Other applications include wound dressings, biomedical adhesives and tissue scaffolds. Use in drug delivery is a further application.

Diseases of the lens material of the eye are often in the form of cataracts. The ideal cataract procedure is considered to be one where the lens capsule bag is maintained with the cataractous lens material removed through a small opening in the capsule. The residual lens epithelial cells are removed chemically and/or with ultrasound or lasers. A biocompatible material with appropriate optical clarity, refractive index and mechanical properties is inserted into the capsular bag to restore the qualities of the original crystalline lens. The desired refractive index is 1.41.

There have been recent advances in methods of inserting intraocular lens. For example, U.S. Pat. No. 5,772,667 assigned to Pharmacia Lovision Inc, discloses a novel intraocular lens injector. This device compresses an intraocular lens by rolling the lens into a tight spiral. The device then injects the compressed lens through a relatively small incision in the eye, approximately 2-3 millimeters in length, resulting from a phacoemulsification procedure. The intraocular lens is inserted into a receiving channel of the injector device in an uncompressed state and is urged into a cylindrical passageway. As the intraocular lens advances into the cylindrical passageway, the lens rolls upon itself into a tightly rolled spiral within the confines of the cylindrical passageway. An insertion rod is then inserted into an open end of the cylindrical passageway and advances the compressed lens down the passageway. As the lens exits the passageway and enters the eye, the lens will expand back to its uncompressed state.

To avoid the need for such injection devices, it has been proposed that intraocular lenses be formed in situ after being injected as a liquid flowable form into the lens capsule bag. However, while this concept is attractive in that smaller incisions would be required, it raises further difficulties in that further chemical reactions are required to cure the injectable material and these are required to be not harmful to the patient. It is also a requirement that the chemical reactions can take place over a relatively short time under mild reaction conditions. It is desirable that the reaction is also not significantly inhibited by oxygen. A still further requirement is that no by-products or residues are produced that may have an adverse biological effect on the patient.

As adults age the accommodative power of the eye decreases leading to the onset of presbyopia. This age-related decrease in accommodative power is believed to be caused by a decrease in the elasticity of the lens material. This decrease is probably caused by cross-linking of the lens material. Thus the loss of accommodation results from a change in elasticity rather than a decrease in the action of the ciliary muscles. The replacement of the original lens with a synthetic polymer having the elasticity equivalent to the lens of a young adult offers the prospect of being able to use a surgical procedure to replace the need for glasses to correct presbyopia.

U.S. Pat. No. 5,079,319 assigned to Ciba-Geigy Corporation discloses vinyl unsaturated macromonomers that are prepared via a two stage process. In the first stage of this process copolymers are prepared by addition polymerisation of ethylenically unsaturated monomers. The monomers are selected such that the polymer chain includes polysiloxane units pendant from a carbon backbone. Ethylenic unsaturation is introduced into the copolymer in the second stage by reaction of an active hydrogen in the polymer chain with an unsaturated isocyanate. The unsaturated macromonomer so formed may be subsequently crosslinked in a mould to form contact lenses. This invention is described as being an improvement over U.S. Pat. No. 4,605,712 which has a common assignee. The improvement is described as being the ability to introduce higher concentrations of siloxane groups without the problems of phase-separation and opacity associated with the compositions of U.S. Pat. No. 4,605,712. U.S. Pat. No. 5,079,319 asserts that addition polymerisation in the first stage leads to more random introduction of siloxane groups and thus the avoidance of large incompatible domains.

Silicones containing pendant (meth)acrylic or (meth)acrylamide groups are particularly suitable for rapid crosslinking using radical photoinitiating systems. U.S. Pat. No. 4,563,539 assigned to Dow Corning Corporation, discloses the synthesis of acrylofunctional siloxanes.

International Publication No. WO99/47185 in the name of Pharmacia & Upjohn Groningen BV proposes intraocular compositions comprising aqueous dispersions of polymerisable microgels. This application relies upon the microgel structure to obtain the rapid crosslinking required for intraocular lens procedures. The invention of this application is distinguished from this invention as it uses oligomers and solution polymers. The citation claims that it is not possible to achieve the required balance of speed of crosslinking, refractive index and mechanical properties necessary for intraocular procedures with such polymers.

SUMMARY OF THE INVENTION

This invention provides in one form an ethylenically unsaturated macromonomer comprising units of Formula I:

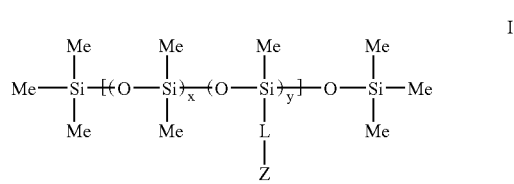

where
- L is a linker group
- Z is an ethylenically unsaturated free radical polymerisable group
- y is $\geq 2$
- x is $\geq 5$ and wherein the ethylenically unsaturated groups are provided by (meth)acrylamide moieties.

The linker group, L, functions as a spacing group which allows the required ethylenic unsaturated group Z to be attached to the copolymer backbone. It may be a linear, branched or cyclic hydro carbyl chain. It may contain hetero atoms as well as carbonyl and other substituted atoms.

In an alternative form this invention provides an ethylenically unsaturated macromonomer comprising units of Formula I wherein the molecular weight of the macromonomer is in the range 3,000-80,000, and wherein the ethylenically unsaturated groups are provided by (meth)acrylamide, (meth)acrylate and styrenic moieties.

In a further alternative form this invention provides an ethylenically unsaturated macromonomer comprising units of Formula I wherein the macromonomer has a viscosity at 25° C. in the range 1,000-20,000 cSt, and more preferably 1,000-10,000 cSt and after polymerisation has an E modulus in the range 0.01-100 kPa, preferably 0.1-10 kPa and more preferably 0.5-5 kPa.

In an alternative embodiment this invention provides polymers for biomedical application wherein polymers are polymerised from macromonomers as defined above.

In a still further alternative form this invention provides a method of preparing intraocular lenses in situ by injecting a flowable macromonomer composition of Formula I into a lens capsule bag where:
- L is a linker group;
- Z is an ethylenically unsaturated free radical polymerisable group;
- y is $\geq 2$ and
- x is $\geq 5$ and wherein the macromonomer has a viscosity at 25° C. in the range 1,000-20,000 cSt, and more preferably 1,000-10,000 cSt and polymerising the macromonomer to provide a polymer having an E modulus in the range 0.01-100 kPa, preferably 0.1-10 kPa and more preferably 0.5-5 kPa.

In a further embodiment this invention provides a method of treating presbyopia by making an incision into the cornea of a patient, removing the lens material and injecting a flowable macromonomer composition of Formula I where the macromonomer has a viscosity at 25° C. in the range 1,000-20,000 cSt, and more preferably 1,000-10,000 Cst and polymerising the macromonomer to provide a polymer having an E modulus in the range 0.01-100 kPa, preferably 0.1-10 kPa and more preferably 0.5-5 kPa.

DETAILED DESCRIPTION OF THE INVENTION

The most effective process for producing the preferred (meth)acrylamide-based macromonomers involves the attachment of acrylamide functional groups to poly(dimethylsiloxane-co-aminoalkylsiloxane) copolymers by reaction with 2-vinyl-4,4-dimethylazlactone in solution as set out below in the scheme of reaction.

However, treatment of the poly(dimethylsiloxane-co-aminoalkylsiloxane) copolymers with acryloyl chloride or other such reagents is an alternative means of synthesis.

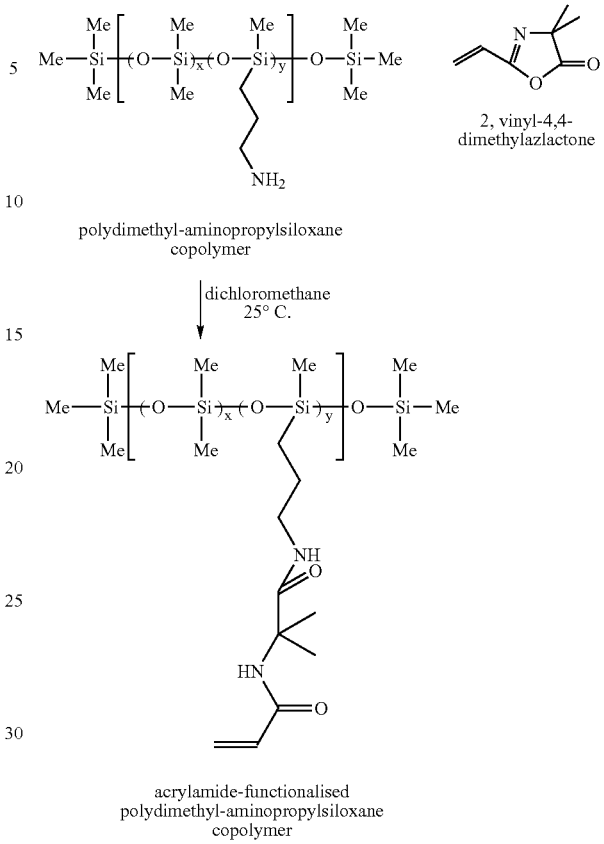

The macromonomers set out in the above scheme of reaction as well as in Formula I are preferably random copolymers. However block type copolymers also fall within the scope of the present invention.

While generally the compositions of the present invention do not usually involve the use of other macromonomers, these may be optionally included. This can be an advantage when the refractive index or viscosity needs to be adjusted. Preferably the compositions comprise at least 50%, more preferably at least 80%, by weight of macromonomers as defined in the present invention.

The macromonomers of this invention may be polymerised by free radical polymerisation to form crosslinked or cured polymers. The mechanical and optical properties of the polymers are preferably matched to those of the natural biological material. In the case of lens material for the eye the refractive index should be close to 1.41. The modulus (E) of the polymer is measured by a Bohlin controlled stress rheometer in the range 0.01-100 kPa, preferably 0.1-10 kPa and most preferably 0.5-5 kPa. The E modulus is influenced by the number of ethylenically unsaturated groups per macromonomer and also the spacing of the ethylenically unsaturated groups. Generally as the number of ethylenically unsaturated groups per macromonomer molecule increases or the spacing between ethylenically unsaturated groups decreases the elasticity of the cured polymer decreases.

The crosslinking process is preferably carried out in such a way that the macromonomer comprising cross-linkable groups is free or essentially free from undesired constituents, in particular from monomeric, oligomeric or polymeric starting compounds used for the preparation of the cross-linkable macromonomer. The polymer product should also be free from by-products formed during the preparation of the crosslinked polymer. The macromonomer is preferably used without the addition of a comonomer although this is allowed.

In the case of photo cross-linking, it is expedient to add an initiator which is capable of initiating free-radical crosslinking. Examples thereof are known to the person skilled in the art; suitable photoinitiators which may be mentioned specifically are benzoins, such as benzoin, benzoin ethers, such as benzoin methyl ether, benzoin ethyl ether, benzoin isopropyl ether and benzoin phenyl ether, and benzoin acetate; acetophenones, such as acetophenone, 2,2-dimethoxyacetophenone and 1,1-dichloroacetophenone; benzil, benzil ketals, such as benzil dimethyl ketal and benzil diethyl ketal, camphorquinone, anthraquinones, such as 2-methylanthraquinone, 2-ethylanthraquinone, 2-tert-butylanthraquinone, 1-chloroanthraquinone and 2-amylanthraquinone; furthermore triphenylphosphine, benzoylphosphine oxides, for example 2,4,6-trimethylbenzoyl-diphenylphosphine oxide, benzophenones, such as benzophenone and 4,4'-bis(N,N-dimethylamino)benzophenone; thioxanthones and xanthenes; acridine derivatives; phenazine derivatives; quinoxaline derivatives and 1-phenyl-1,2-propanedione 2-O-benzoyl oxime; 1-aminophenyl ketones and 1-hydroxyphenyl ketones, such as 1-hydroxycyclohexylphenyl ketone, phenyl 1-hydroxyisopropyl ketone, 4-isopropylphenyl 1-hydroxyisopropyl 1-hydroxyisopropyl ketone, 2-hydroxy-1-[4-2(-hydroxyethoxy)phenyl]-2-methylpropan-1-one, 1-phenyl-2-hydroxy-2-methylpropan-1-one, and 2,2-dimethoxy-1,2-diphenylethanone, all of which are known compounds.

Particularly suitable photoinitiators, which are usually used with UV lamps as light sources, are acetophenones, such as 2,2-dialkoxybenzophenones and hydroxyphenyl ketones, in particular the initiators known under the trade names IRGACURE®819 and IRGACURE®184. A particularly preferred photoinitiator is IRGACURE®651.

Another class of photoinitiators usually employed when argon ion lasers are used are benzil ketals, for example benzil dimethyl ketal. The photoinitiators are added in effective amounts, expediently in amounts from about 0.05 to about 2.0% by weight, in particular from 0.1 to 0.5% by weight, based on the total amount of cross-linkable macromonomer.

The resultant cross-linkable macromonomer can be introduced into a mould using methods known per se, such as, in particular, conventional metering, for example dropwise. Alternatively, the macromonomers may be cured in situ, as for example in the case of an injectable lens. In this case the macromonomer is cured or crosslinked in the lens capsule after injection.

The cross-linkable macromonomers which are suitable in accordance with the invention can be crosslinked by irradiation with ionising or actinic radiation, for example electron beams, X-rays, UV or VIS light, ie electromagnetic radiation or particle radiation having a wavelength in the range from about 280 to 650 nm. Also suitable are UV lamps, He/Dc, argon ion or nitrogen or metal vapour or NdYAG laser beams with multiplied frequency. It is known to the person skilled in the art that each selected light source requires selection and, if necessary, sensitisation of the suitable photoinitiator. It has been recognised that in most cases the depth of penetration of the radiation into the cross-linkable macromonomer and the rate of curing are in direct correlation with the absorption coefficient and concentration of the photoinitiator. As well as photoinitiation, redox and thermal initiators may be used satisfactorily.

If desired, the crosslinking can also be initiated thermally. It should be emphasised that the crosslinking can take place in a very short time in accordance with the invention, for example, in less than five minutes, preferably in less than one minute, more preferably in less than 30 seconds. It will be appreciated that while the macromonomers of this invention may be used alone to form the lenses and other biocompatible materials, other materials may also be present. For example, diluents may be present as well as other monomers including other macromonomers. When used as an injectable material the macromonomers should have a viscosity in the range 1,000-20,000 cSt and more preferably 1,000-10,000 cSt at 25° C. Instruments such as the Brookfield rheometer or the Bohlin controlled stress rheometer may be conveniently used for measurement.

The invention will be further described by reference to the following examples where all parts are expressed as parts by weight.

EXAMPLE 1

This example illustrates the preparation of an acrylamide macromonomer.

An acrylamidoorganosilicon macromonomer of Formula I, where y=3, x=60, and having a molecular weight in the range from 4,000 to 5,000, containing three acrylamido radicals A, having the formula —C(O)—C(CH$_3$)$_2$—NHC(O)CH=CH$_2$ was prepared as follows:

(CH$_3$)$_3$SiO((CH$_3$)$_2$SiO)$_x$(O CH$_3$Si(CH$_2$)$_3$NHA)$_y$OSi(CH$_3$)$_3$     I

Into a 25 ml flask equipped with a stirrer bar and containing 10 ml dry dichloromethane is placed 2.4 g of a commercially available aminopropylmethylsiloxane-dimethysiloxane copolymer (available from Gelest, Inc., Tullytown, Pa. as Product AMS-162). To this is added 0.23 g of distilled 2-vinyl-4,4-dimethylazlactone. The reaction mixture is stirred for 18 hours, after which the infra red spectrum is recorded to confirm complete consumption of the vinylazlactone. Dichloromethane solvent is then removed in vacuo to yield a macromonomer of viscosity 250 centiStokes (cSt).

EXAMPLE 2

This example illustrates the preparation of a crosslinked polymer using the macromonomer prepared in Example 1.

The acrylamide-functionalised siloxane and Irgacure 651 photoinitiator (Ciba Speciality Chemicals) were separately dissolved in chloroform in the proportions given below. The solutions were combined and the chloroform was removed in vacuo. The following example was placed into polypropylene moulds (designed to give a flat polymeric disc of 20.7 mm diameter and 1.0 mm depth) and polymerised for ten minutes under irradiation from a 365 nm UV lamp. All parts are by weight.

| | |
|---|---|
| Macromonomer of Formula I (x = 60, y = 3) | 100 parts |
| Irgacure 651 | 0.3 parts |

After polymerisation was complete, a transparent, rubbery polymer disc was removed from the moulds. The shear modulus of the polymer was measured with a Bohlin controlled stress rheometer (CS-10) as 220 kPa.

EXAMPLE 3

This example illustrates that the synthetic procedure outlined in Example 1 may be extended to other amino group containing polydimethylsiloxane copolymers.

| Macro monomer | Mole % amino groups | Molecular weight | Percent azlactone substitution of amino groups | Shear Modulus (kPa) after polymerisation | Viscosity (cSt) | r.i. |
|---|---|---|---|---|---|---|
| 2A[1] | 2-4 | 28,000-32,000 | 47% | 85 | 14,600 | 1.4132 |
| 2B[1] | 2-4 | 28,000-32,000 | 25% | 2.5 | 250 | 1.4239 |

[1]Prepared from Aminoethylaminopropyl Methylsiloxane-Dimethylsiloxane Copolymer (Gelest Systems, Inc. Product AMS-233).

EXAMPLE 4

This example illustrates the preparation of cured polymers from macromonomers prepared according to Example 3.

Macromonomers 2A and 2B were placed into polypropylene moulds and polymerised for ten minutes under irradiation from a 365 nm UV lamp. 100 parts Macromonomer and 0.3 parts Irgacure 651 photoinitiator were used in both examples. The difference in shear moduli for examples 2A and 2B shows that the mechanical properties of the polymer can be varied as desired by changing the degree of acrylamide substitution.

EXAMPLE 5

This example illustrates the preparation of a macromonomer where the ethylenically unsaturated groups are provided by acrylate moieties and the polymerisation of this macromonomer to a polymer.

A silicone acrylate compound of Formula II, where the average value of x=790, and the average value of y=60, and the molecular weight of the macromonomer is 62,000 containing an average of 60 acrylate radicals, A, having the formula —O—CO—CH=$CH_2$, was prepared as follows

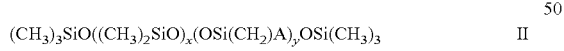

$(CH_3)_3SiO((CH_3)_2SiO)_x(OSi(CH_2)A)_yOSi(CH_3)_3$    II

In a 250 ml round-bottom flask equipped with a reflux condenser and drying tube, methylhydrosiloxane-dimethylsiloxane copolymer (available from Gelest, Inc., Tullytown, Pa. as Product HMS-064) (20.03 g, 18.91 mmol SiH groups) and allyl chloride (Aldrich, 1.45 g, 18.9 mmol) were dissolved in 50 ml dry toluene and then 95 microliters of a 0.02 M solution of hexachloroplatinic acid in isopropanol was added. The reaction mixture was then stirred for 18 h at 80° C. Consumption of the silicone hydride (SiH) groups was verified by treating an aliquot of the reaction mixture with ethanolic KOH solution—no hydrogen evolution was observed.

The reaction mixture was then cooled to 5° C. and butylated hydroxytoluene (25 mg) and dry pyridine (1.5 g, 18.96 mmol) were added. A solution of 2-hydroxyethyl acrylate (2.196 g, 18.90 mmol) in 10 ml dry toluene was then added dropwise at such a rate so as to maintain the reaction temperature below 5° C. The macromonomer was washed twice with methanol (100 ml) and then left for four days in a dark environment. Irgacure 651 photoinitiator (Ciba Speciality Chemicals) was dissolved in dry toluene and combined with the acrylate-functionalised siloxane in dry toluene to give a concentration of photoinitiator to macromonomer identical to that for Example 4.

The formulation (viscosity 7,3000 cSt) was then placed into polypropylene moulds designed to give a flat polymeric disc (refractive index 1.4107) of 20.7 mm diameter and 1.0 mm depth, (obtained from CIBA Vision, Atlanta) and polymerised for ten minutes under irradiation from a 365 nm UV lamp. After polymerisation was complete, a transparent, rubbery polymer disc (refractive index 1.4107) was removed from the mould. The shear modulus of the polymer was measured with a Bohlin controlled stress rheometer (CS-10) as 44.5 kPa.

EXAMPLE 6

This example illustrates the preparation of a macromonomer where the ethylenically unsaturated groups are provided by methacrylate moieties and the polymerisation of this macromonomer to a polymer.

A silicone methacrylate compound of Formula III, where the average value of x=730, and the average value of y=7, and the molecular weight of the macromonomer is 55,000 containing an average of 7 methacrylate radicals, A, having the formula —O—CO—($CH_3$)CH=$CH_2$, was prepared as follows:

$(CH_3)_3SiO((CH_3)_2SiO)_x(O(CH_3)Si(CH_2)_3A)_yOSi(CH_3)_3$    III

Into a 50 ml flask equipped with a stirrer bar and containing 20 ml dry toluene is placed 2.6543 g (0.36 mmol SiH groups) of a commercially available methylhydrosiloxane-dimethylsiloxane copolymer (available from Gelest, Inc., Tullytown, Pa. as Product HMS-013) and 0.2 g (1.59 mmol) of allyl methacrylate. 100 microliters of a 0.02 M solution of hexachloroplatinic acid in isopropanol is then added. The reaction mixture is stirred for 72 hours, after which the $^1H$ NMR spectrum is recorded to confirm complete reaction of the silicone hydride group (δ=4.7 ppm).

The methacrylate-functionalised siloxane and Irgacure 651 photoinitiator (Ciba Specialty Chemicals) (in proportions identical to that used in Example 4) were separately dissolved in toluene. The solutions were combined and the toluene removed in vacuo, to yield a macromonomer of viscosity 3,300 cSt.

The formulation was then placed into polypropylene moulds (designed to give a flat polymeric disc of 20.7 mm diameter and 1.0 mm depth, obtained from CIBA Vision, Atlanta) and polymerised for ten minutes under irradiation from a 365 nm UV lamp. After polymerisation was complete, a transparent, rubbery polymer disc (refractive index 1.4086) was removed from the mould. The shear modulus of the polymer was measured with a Bohlin controlled stress rheometer (CS-10) as 22.5 kPa.

EXAMPLE 7

This example illustrates the in vivo use of macromonomers according to this invention as intraocular lenses.

After initial softening by techniques such as phacoemulsification, endolenticular fragmentation, laser phacolysis, the existing lens material of a patient is removed via aspiration through a small (less than 1.2 mm, but preferably equal to or less than 0.5 mm) capsulorhexis at the periphery of the lens, with minimal damage to the capsule and peripheral tissue. The interior of the capsular bag is then cleaned and aspirated to remove cellular debris which may contribute to opacification of the posterior capsule subsequent to surgery—a number of viscoelastic fluids e.g. hyaluronic acid may be used to flush the lens capsule. Other techniques (e.g. photodynamic therapy) may be used at this time to provide an additional means of decreasing the incidence of posterior capsule opacification.

The macromonomer from Example 1 that is to form the substitute lens material is then introduced into the capsular bag through the capsulorhexis via a narrow gauge cannula. Optionally, an additional valve device may be positioned on the exterior of the empty lens capsule to enable injection of the substitute lens material without leakage prior to cure of the material. After refilling of the lens capsule, the material is cured by UV irradiation. Other means including, but not limited to visible irradiation, thermal or redox reaction could also have been used.

The incision in the cornea is sutured and allowed to heal.

The invention claimed is:

1. An ethylenically unsaturated macromonomer comprising a random or block copolymer of Formula I:

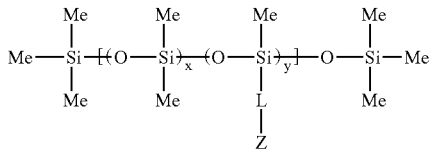

where
L is a linear, branched, or cyclic hydrocarbyl chain, optionally containing heteroatoms or carbonyl
Z is an ethylenically unsaturated free radical polymerizable group
y is ≧2
x is ≧200
and wherein the ethylenically unsaturated groups are provided by a moiety selected from the group consisting of (meth)acrylamide, (meth)acrylate and styrenic moieties wherein x is at least 100 times greater than y; and after polymerization to form a polymer, the polymer has an E modulus in the range of 0.01-100 kPa.

2. An ethylenically unsaturated macromonomer according to claim 1 in which the ratio of x:y is between about 100:1 and about 200:1.

3. An ethylenically unsaturated macromonomer according to claim 1 wherein the molecular weight of the macromonomer is in the range 3,000-80,000.

4. An ethylenically unsaturated macromonomer according to claim 1 in which —L—Z is an aminoalkyl or hydroxyalkyl group functionalized with (meth)acrylate or (meth)acrylamide.

5. An ethylenically unsaturated macromonomer according to claim 1 wherein the macromonomer is prepared by reacting a mixture comprising polydimethyl-aminopropylsiloxane co-polymer and 2-vinyl-4,4-dimethylazlactone.

6. An ethylenically unsaturated macromonomer according to claim 1 wherein the macromonomer has a viscosity at 25° C. in the range 1,000-20,000 cSt.

7. An ethylenically unsaturated macromonomer according to claim 1 wherein the macromonomer has a viscosity at 25° C. in the range 1,000-10,000 cSt.

8. An ethylenically unsaturated macromonomer according to claim 1 wherein after polymerization to form a polymer, the polymer has an E modulus in the range of 0.1-10 kPa.

9. An ethylenically unsaturated macromonomer according to claim 1 wherein after polymerization to form a polymer, the polymer has an E modulus in the range of 0.5-5 kPa.

10. An ethylenically unsaturated macromonomer according to claim 1 wherein after polymerization to form a polymer, the polymer has an E modulus in the range of 0.1-5 kPa.

11. An ethylenically unsaturated macromonomer according to claim 1 wherein after polymerization the polymer has a refractive index in the range 1.39-1.44.

12. An ethylenically unsaturated macromonomer comprising a random or block copolymer of Formula I:

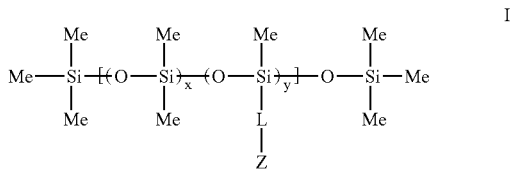

where
L is a linear, branched, or cyclic hydrocarbyl chain, optionally containing heteroatoms or carbonyl
Z is an ethylenically unsaturated free radical polymerizable group
y is ≧2
x is ≧200
and wherein the ethylenically unsaturated groups are provided by a moiety selected from the group consisting of (meth)acrylamide, (meth)acrylate and styrenic moieties and wherein after polymerization to form a polymer, the polymer has an E modulus in the range of 0.1-10 kPa.

13. An ethylenically unsaturated macromonomer according to claim 12 in which —L—Z is an aminoalkyl or hydroxyalkyl group functionalized with (meth)acrylate or (meth)acrylamide.

14. A method of preparing intraocular lenses in situ by injecting a flowable macromonomer according to claim 1 into a lens capsular bag and polymerizing the macromonomer to provide a polymer, wherein the macromonomer has a viscosity at 25° C. in the range 1,000-20,000 cSt.

15. A method of treating presbyopia by removing the lens material and injecting a flowable macromonomer according to claim 1 into a lens capsular bag and polymerizing the macromonomer to provide a polymer, wherein the macromonomer has a viscosity at 25° C. in the range 1,000-20,000 cSt.

16. A method of treating presbyopia by removing the lens material and injecting a flowable macromonomer according to claim 12 into a lens capsular bag and polymerizing the macromonomer to provide a polymer, wherein the macromonomer has a viscosity at 25° C. in the range 1,000-20,000 cSt.

17. A method according to claim 14 further comprising adding a photoinitiator.

18. A method according to claim 17 in which the amount of photoinitiator is between 0.05% and 2% by weight.

19. A polymer comprising macromonomers according to claim 1.

20. A polymer comprising macromonomers according to claim 12.

21. A polymer according to claim 19 in which the macromonomers comprise at least 50% by weight.

22. A polymer according to claim 20 in which the macromonomers comprise at least 50% by weight.

23. A polymer according to claim 19 in which the macromonomers comprise at least 80% by weight.

24. A polymer according to claim 21 further comprising other macromonomers to adjust the refractive index of the polymer.

25. A polymer according to claim 21 further comprising other macromonomers to adjust the viscosity of the polymer.

26. An intraocular lens comprising a polymer according to claim 22.

27. An intraocular lens comprising a polymer according to claim 22.

* * * * *